(12) United States Patent
Hsieh et al.

(10) Patent No.: US 6,393,090 B1
(45) Date of Patent: May 21, 2002

(54) COMPUTED TOMOGRAPHY SCOUT IMAGES WITH DEPTH INFORMATION

(75) Inventors: Jiang Hsieh, Brookfield; Robert F. Senzig, Germantown, both of WI (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/410,161

(22) Filed: Sep. 30, 1999

Related U.S. Application Data
(60) Provisional application No. 60/114,334, filed on Dec. 31, 1998.

(51) Int. Cl.[7] ............................................. G01N 23/00
(52) U.S. Cl. ............................................ 378/4; 378/20
(58) Field of Search ....................................... 378/4, 20

(56) References Cited

U.S. PATENT DOCUMENTS

| | | |
|---|---|---|
| 4,382,184 A | 5/1983 | Wernikoff |
| 4,994,965 A | 2/1991 | Crawford et al. |
| 5,490,516 A | 2/1996 | Hutson |
| 5,647,360 A | 7/1997 | Bani-Hashemi et al. |
| 5,682,887 A | 11/1997 | Xu et al. |
| 6,028,907 A * | 2/2000 | Adler et al. .................... 378/4 |
| 6,041,097 A | 3/2000 | Roos et al. |
| 6,154,516 A | 11/2000 | Heuscher et al. |
| 6,185,271 B1 | 2/2001 | Kinsinger |

* cited by examiner

*Primary Examiner*—Craig E. Church
(74) *Attorney, Agent, or Firm*—Carl B. Horton, Esq.; Armstrong Teasdale LLP

(57) ABSTRACT

The present invention, in one form, is a method for generating depth information images of an object using a computed tomography system by performing multiple scout scans of the object, generating a scout image for each scout scan, and displaying the scout images from each scout scan at least once. As a result, the multiple scout images contain depth information of anatomical objects and 3D images are rapidly generated without increasing the cost of the system.

24 Claims, 3 Drawing Sheets

COMPUTED TOMOGRAPHY SCOUT IMAGES WITH DEPTH INFORMATION

CROSS REFERENCE TO RELATED APPLICATION

This application claims the benefit of U.S. Provisional Application No. 60/114,334, filed Dec. 31, 1998, which is hereby incorporated by reference in its entirety.

BACKGROUND OF THE INVENTION

This invention relates generally to computed tomography (CT) imaging and more particularly, to generating depth information scout images.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

In at least one known imaging system, a single scout image is generated by fixing the position of the x-ray source and translating the object in a z-axis direction. As a result, the scout image is similar to a plain radiography image. Using the scout image, an operator may identify anatomical landmarks so that proper techniques may be selected for different areas of the object. However, as a result of generating the scout image from a single projection angle, no depth information regarding the object anatomy is provided.

It is therefore seen to be desirable to provide a CT system which provides scout images having depth information of the object. It is also desirable to generate a shaded 3D image of the scanned object.

BRIEF SUMMARY OF THE INVENTION

There is therefore provided, in one embodiment of the present invention, a method for generating depth information images of an object using a computed tomography system by performing multiple scout scans of the object, generating a scout image for each scout scan, and displaying the scout images from each scout scan at least once.

The above described embodiment and others described herein generate scout images having depth information of anatomical objects. In addition, 3D images are rapidly generated without increasing the cost of the system.

DETAILED DESCRIPTION OF THE INVENTION

Figure 1:
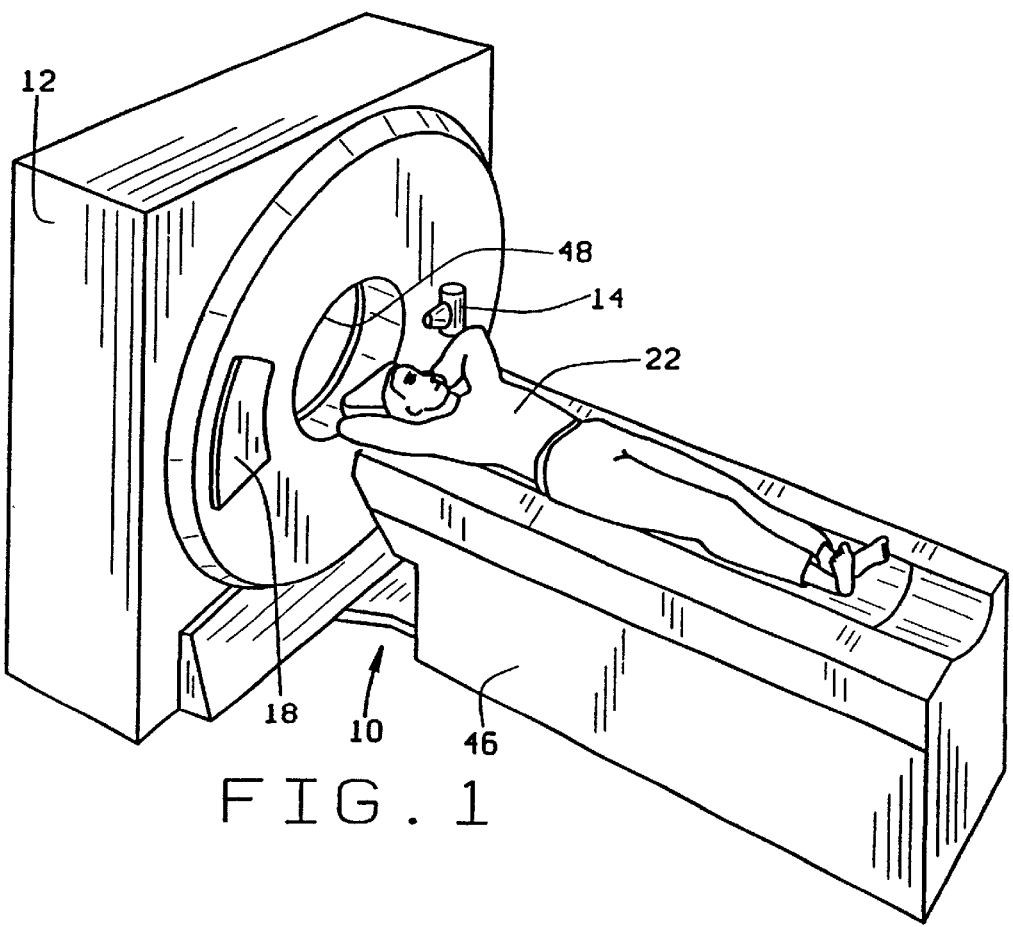
FIG. 1 is a pictorial view of a C-T imaging system.
Figure 2:
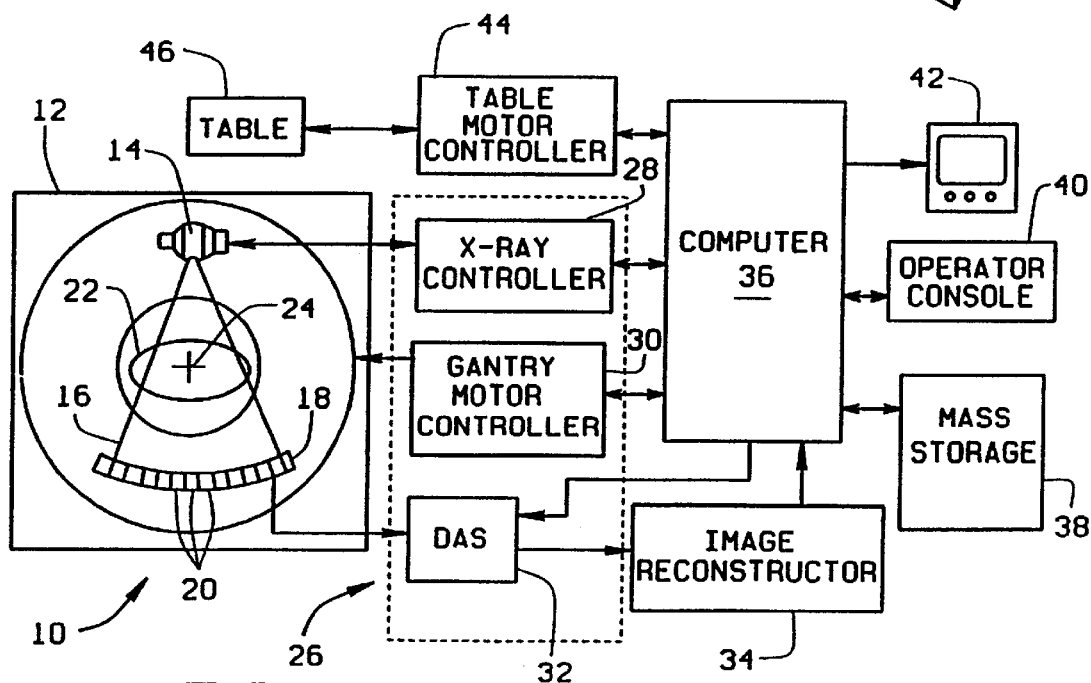
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment of the present invention, system 10 performs a plurality of scout scans to generate depth information scout images of an object. More specifically, in order to generate at least one depth information scout image, system 10 performs each scout scan at a different projection angle with respect to the scanned object, i.e., patient 22.

Particularly, after patient 22 is positioned on table 46, the position of gantry 12 is adjusted so that source 14 and detector array 18 are aligned along a first projection angle, or scout angle, with respect to patient 22. As patient 22 is translated along a z-axis at a constant speed, x-ray beams 16 are emitted from the fixed position source 14 so that first scout, or projection, data is collected, or generated, from detector array 18. At least a second scout scan is then performed by adjusting the position of x-ray source 14 with respect to patient 22. Particularly, the position of gantry 12 is adjusted so that source 14 and detector array 18 are aligned along a second projection angle, or scout angle, with respect to patient 22. As patient 22 is translated along the z-axis at a constant speed, x-ray beams 16 are emitted from source 14 so that second scout, or projection, data is collected from detector array 18.

The obtained scout scan data is then processed to generate at least one scout image. More specifically and in one embodiment, first projection data is processed, in a manner known in the art, to generate a first scout image. Scout images for each additional scout scan are then generated from the respective scout scan data. Each scout scan image is displayed to provide depth information regarding the anatomy of patient 22. Specifically, each scout scan is sequentially displayed, for example on display 42, at least once. In one embodiment, where two scout images are generated, the first scout image is displayed and then the second image is displayed. To generate a 3D effect image, system 10 rapidly alternates between the two scout images. For example, each scout image may be displayed in a rapid cine sequence, i.e., display of first image, second image, first image, second image, etc. on display 42 so that a 3D visual effect is generated. In addition, where more than two scout images are generated, each image may be sequentially displayed on display 42, or at least any two selected scan images may be displayed so that the 3D visual effect is generated.

As a result of alternating between each scout image, the scanned object will appear to rock, or shift, back and forth. As the scout images are displayed on display 42, integration by the eyes of the operator provide relative spatial location information of different anatomical parts. This spatial location information represents the 3D visual effect image.

In one embodiment, to generate at least one depth information scout image, system 10 performs two scout scans. Specifically, a first scout scan is performed at a first projection angle and a second scout scan is performed at a second projection angle, wherein the first projection angle is not equal to the second projection angle. For example, by performing the first scout scan at a 70 degree projection angle and the second scout scan at a 90 degree projection angle, a depth information scout image may be generated. After processing the scan data to generate a first scout image and a second scout image, the scout images may be alternatingly displayed on display 42. In one embodiment, the projection angles of each scout scan may be adjusted, or altered, so that the best visual effects are obtained. In addition, where more than two scout images are generated, each image may be sequentially displayed on display 42, or at least any two selected scan images may be displayed.

Figure 3:
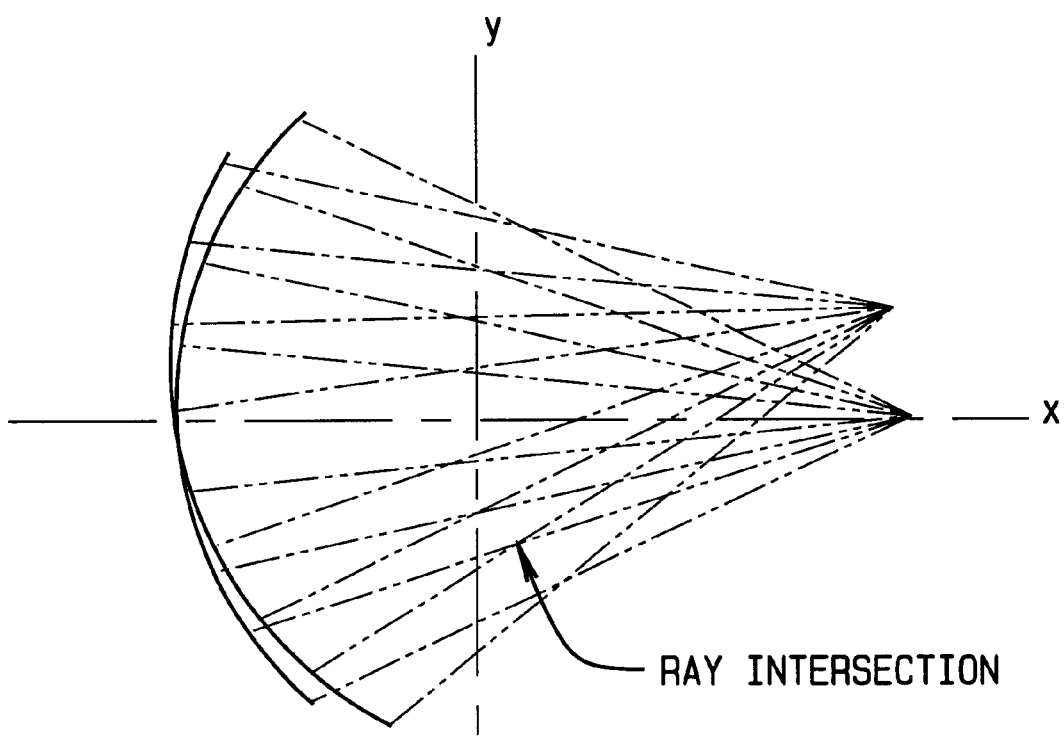
FIG. 3 is pictorial view of location information based on the intersection of two scout scans.
Figure 4:
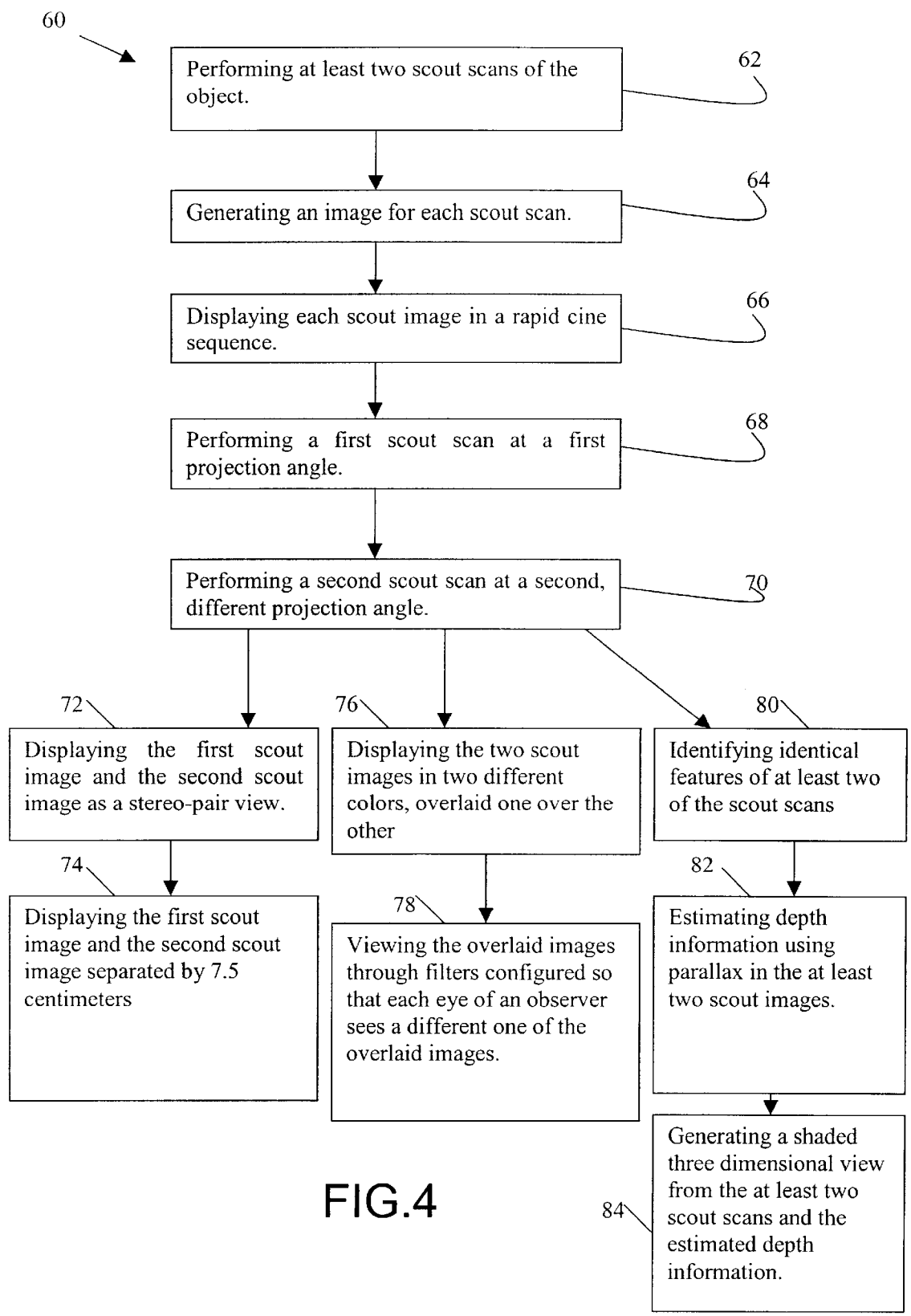
FIG. 4 is a flow chart illustrating a method for generating depth information from multiple scout images of an object acquired by a CT scanner according to the invention.

In another embodiment, the scout scan data is processed to produce at least one depth dependent shading, or intensity, scout image. More specifically and as shown in FIG. 3, a 3D shaded image is generated using the data from the intersection of at least two scout scans. Particularly, using known bi-plane reconstruction algorithms, the shading of the 3D image is determined by the attenuation of the intersection of the scout scans. As a result, the 3D images may be used to identify the specific location of highly attenuating objects within the scanned object.

In another embodiment, stereo-pair views are used to communicate depth information. For example, two scout images generated after processing scan data taken at two different angles are placed side by side as a stereo-pair view (e.g. 7.5 centimeters apart). An experienced viewer looks straight ahead and allows the brain to fuse the two images without optical aids. This is often called stereoscopy.

In another embodiment, two scout images generated after processing the scan data taken at two different angles are overlaid and displayed simultaneously using different colors, for example, red and green or red and blue, for each image. To view the combined image and perceive depth information, the viewer uses glasses with, for example, a red filter in front of one eye and a green or blue filter in front of the other eye so that each eye sees only one of the scout images. The human brain sorts out the depth information.

In yet another embodiment, an algorithm performs the fusion of at least two scout scans into one viewable scout image instead of the human brain. The algorithm identifies the same features in the different scans and estimates depth information from the parallax in the scout scans.

The above described system generates depth information scout images of anatomical objects. In addition, shaded 3D images are rapidly generated without increasing the cost of the system.

Although the invention has been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Accordingly, the spirit and scope of the invention are to be limited only by the terms of the appended claims.

What is claimed is:

1. A method for generating depth information images of an object using a computed tomography (CT) imaging system, the CT system including an x-ray tube for emitting x-ray beams and a detector aligned with the x-ray tube for receiving the x-ray beams, said method comprising the steps of:

performing at least two scout scans of the object;
   generating an image for each scout scan; and
   displaying each scout image in a rapid cine sequence.

2. A method in accordance with claim 1 wherein performing at least two scout scans of the object comprises the steps of:

performing a first scout scan at a first projection angle; and
   performing a second scout scan at a second, different projection angle.

3. A method in accordance with claim 2 wherein displaying each scout image comprises the steps of:

a) sequentially displaying each scout image; and
   b) repeating, at least once, said step of sequentially displaying each scout image.

4. A method in accordance with claim 2 further comprising the steps of:

identifying identical features of at least two of the scout scans;

estimating depth information using parallax in the at least two scout images; and generating a shaded three dimensional view from the at least two scout scans and the estimated depth information.

5. A method in accordance with claim 2 wherein performing at least two scout scans of the object comprises the step of scanning the object to obtain projection data for each scout scan.

6. A method in accordance with claim 5 wherein generating an image for each scout scan comprises the step of processing the obtained projection data to generate a scout image for each scout scan.

7. A method in accordance with claim 5 wherein generating an image for each scout scan comprises the step of processing the obtained projection data to generate at least one depth information image.

8. A method in accordance with claim 5 wherein generating an image for each scout scan comprises the step of processing the obtained projection data to identify highly attenuating objects.

9. A method in accordance with claim 2 wherein displaying each scout scan at least once comprises displaying the first scout image and the second scout image as a stereo-pair view.

10. A method in accordance with claim 9, wherein displaying the first scout scan and the second scout scan as a stereo-pair view comprises displaying first scout image and the second scout image separated by 7.5 centimeters.

11. A method in accordance with claim 2 wherein displaying each scout scan at least once comprises simultaneously displaying the two said scout images in two different colors, overlaid one over the other.

12. A method in accordance with claim 11 further comprising viewing the overlaid images through filters configured so that each eye of an observer sees a different one of the overlaid images.

13. A computed tomography (CT) system for generating depth information images of an object, said CT system comprising an x-ray tube for emitting x-ray beams and a detector aligned with said x-ray tube for receiving said x-ray beams, said system configured to:

perform at least two scout scans of the object;

generate a scout image for each scout scan; and display each scout image in a rapid cine sequence.

14. A system in accordance with claim 13 wherein to perform at least two scout scans of the object, said system configured to:

perform a first scout scan at a first projection angle; and perform a second scout scan at a second, different projection angle.

15. A system in accordance with claim 14 wherein to display each scout image, said system configured to:

a) sequentially display each scout image; and b) repeat, at least once, said sequentially display of each scout image.

16. A system in accordance with claim 14, said system further configured to:

simultaneously display the two said scout images in two different colors, overlaid one over the other.

17. A system in accordance with claim 16 wherein the overlaid images are viewed through filters configured so that each eye of an observer sees a different one of the overlaid images.

18. A system in accordance with claim 14 wherein to perform at least two scout scans of the object, said system configured to scan the object to obtain projection data for each scout scan.

19. A system in accordance with claim 18 wherein to generate an image for each scout scan, said system configured to process the obtained projection data to generate a scout image for each scout scan.

20. A system in accordance with claim 18 wherein to generate an image for each scout scan, said system configured to process the obtained projection data to generate at least one depth information image.

21. A system in accordance with claim 18 wherein to generate an image for each scout scan, said system configured to process the obtained projection data to identify highly attenuating objects.

22. A system in accordance with claim 14 wherein system is further configured to display the first scout image and the second scout image as a stereo-pair view.

23. A system in accordance with claim 22, displaying the first scout scan and the second scout scan as a stereo-pair view comprises displaying first scout image and the second scout image separated by 7.5 centimeters.

24. A system in accordance with claim 14 aid system further configured to:

identify identical features of at least two of the scout scans;

estimate depth information using parallax in the at least two scout images; and generate a shaded three dimensional view from the at least two scout scans and the estimated depth information.

* * * * *

UNITED STATES PATENT AND TRADEMARK OFFICE
CERTIFICATE OF CORRECTION

PATENT NO.    : 6,393,090 B1                                                   Page 1 of 1
DATED         : May 21, 2002
INVENTOR(S)   : Jiang Hsieh et al.

It is certified that error appears in the above-identified patent and that said Letters Patent is hereby corrected as shown below:

Column 6,
Line 40, delete "aid" insert therefor -- said --.

Signed and Sealed this

Fourteenth Day of October, 2003

JAMES E. ROGAN
*Director of the United States Patent and Trademark Office*